US012264966B2

(12) United States Patent
Cai et al.

(10) Patent No.: US 12,264,966 B2
(45) Date of Patent: Apr. 1, 2025

(54) FLUORESCENCE IMAGING PROBE AND HANDHELD IMAGINGPROBER (71) Applicant: NANJING NUOYUAN MEDICAL DEVICES CO., LTD., Jiangsu (CN)

(72) Inventors: Huiming Cai, Nanjing (CN); Ziyang Wang, Nanjing (CN)

(73) Assignee: NANJING NUOYUAN MEDICAL DEVICES CO., LTD., Nanjing (CN)

( * ) Notice: Subject to any disclaimer, the term of this patent is extended or adjusted under 35 U.S.C. 154(b) by 0 days.

(21) Appl. No.: 18/562,332

(22) PCT Filed: Apr. 6, 2023

(86) PCT No.: PCT/CN2023/086671
§ 371 (c)(1),
(2) Date: Nov. 20, 2023

(87) PCT Pub. No.: WO2024/077895
PCT Pub. Date: Apr. 18, 2024

(65) Prior Publication Data
US 2024/0272001 A1 Aug. 15, 2024

(30) Foreign Application Priority Data
Oct. 14, 2022 (CN) .......................... 202211256931.9

(51) Int. Cl.
*G01J 3/44* (2006.01)
*G01J 3/02* (2006.01)
(Continued)

(52) U.S. Cl.
CPC ........... *G01J 3/4406* (2013.01); *G01J 3/0272* (2013.01); *G01J 3/2823* (2013.01); *G01J 2003/1213* (2013.01)

(58) Field of Classification Search
CPC ...... G01J 3/2823; G01J 3/0272; G01J 3/4406; G01J 2003/1213
See application file for complete search history.

(56) References Cited

U.S. PATENT DOCUMENTS

2003/0006385 A1\* 1/2003 Banks ................. G01N 21/643
250/559.4
2010/0301231 A1\* 12/2010 Yamaguchi ........... G01J 3/4406
250/459.1
(Continued)

FOREIGN PATENT DOCUMENTS

CN 102818794 A 12/2012
CN 204731160 U 10/2015
(Continued)

OTHER PUBLICATIONS

English Abstract of cited patent documents.
(Continued)

*Primary Examiner* — Maurice C Smith
(74) *Attorney, Agent, or Firm* — Hemisphere Law, PLLC; Zhigang Ma (57) ABSTRACT

Provided are a fluorescence imaging probe and a handheld imaging prober, relating to the technical field of medical devices. The fluorescence imaging probe includes a dichroic filter and an image detector, the dichroic filter is arranged at an included angle of 45° with a direction of a main optical axis of incident excitation light, the incident excitation light is reflected by the dichroic filter to a target detection position, the reflected incident excitation light excites a fluorescent substance at the target detection position to form fluorescence, a main optical axis of the fluorescence is arranged coaxially with the image detector, the fluorescence is incident to the image detectors through the dichroic filter, and the image detector converts the received fluorescence into an image signal.

9 Claims, 5 Drawing Sheets (51) Int. Cl.
*G01J 3/28* (2006.01)
*G01J 3/12* (2006.01)

(56) References Cited

U.S. PATENT DOCUMENTS

2012/0280144 A1* 11/2012 Guilfoyle .............. G01J 3/0218
                                                         250/206
2018/0314141 A1* 11/2018 Yamakage ........... G03B 21/208

FOREIGN PATENT DOCUMENTS

| CN | 106901683 | A |   | 6/2017  |           |
|----|-----------|---|---|---------|-----------|
| CN | 208140563 | U |   | 11/2018 |           |
| CN | 109288490 | A |   | 2/2019  |           |
| CN | 110007453 | A |   | 7/2019  |           |
| CN | 110132910 | A | * | 8/2019  | G01J 3/2823 |
| CN | 210990151 | U |   | 7/2020  |           |
| CN | 112198654 | A |   | 1/2021  |           |
| CN | 112336457 | A |   | 2/2021  |           |
| CN | 112525870 | A |   | 3/2021  |           |
| CN | 112656370 | A | * | 4/2021  |           |
| CN | 113835208 | A |   | 12/2021 |           |
| CN | 113945904 | A |   | 1/2022  |           |
| CN | 114839172 | A |   | 8/2022  |           |
| CN | 115316961 | A |   | 11/2022 |           |

OTHER PUBLICATIONS

First search of priority application CN202211256931.9.
Jul. 17, 2023 International Search Report of PCTCN2023086671.
Jan. 16, 2023 Notification to Grant Patent Right for Invention of priority application CN202211256931.9.
Jul. 17, 2023 Written Opinion of The International Searching Authority of PCTCN2023086671.
OA1 of priority application of CN202211256931.9.
OA2 of priority application of CN202211256931.9.
English Translation of Allowed Claims of Priority Doc. CN 202211256931.9.

* cited by examiner

FLUORESCENCE IMAGING PROBE AND HANDHELD IMAGINGPROBER

CROSS-REFERENCE TO RELATED APPLICATIONS

This application is a national phase filing under 35 C.F.R. § 371 of and claims priority to PCT Patent Application No. PCT/CN2023/086671, filed on Apr. 6, 2023, which claims the priority benefit under 35 U.S.C. § 119 of Chinese Patent Application No. 202211256931.9, filed on Oct. 14, 2022, the contents of which are hereby incorporated in their entireties by reference.

TECHNICAL FIELD

The present disclosure relates to the technical field of medical devices, and specifically to a fluorescence imaging probe and a handheld imaging prober.

BACKGROUND ART

Molecular imaging refers to nondestructive probing and imaging of living organisms at the cellular and molecular level, such as nuclear magnetic resonance, PET, ultrasound, and optical molecular imaging. As an important imaging modality therein, the optical molecular imaging has become a research hotspot by virtue of advantages such as low costs, high throughput, non-invasion, non-contact, nonionizing radiation, high sensitivity, and high specificity. Excitation fluorescence molecular imaging technology is an important branch of the optical molecular imaging, which excites a fluorescent marker in a living organism using an external light source, the excited fluorescent marker emits fluorescence of a near infrared waveband, and a high-sensitivity prober is used to receive fluorescence information and form a fluorescence image.

Some imaging systems suitable for open surgeries have a relatively large volume and are equipped with a suspended self-balancing arm, and such systems generally have the disadvantages of being bulky and not easy to move, having limited observation angles, and possibly affecting the operation of doctors in open surgeries. In recent years, for this problem, there appear more portable and lightweight handheld open surgical imaging systems, and such systems use an excitation light illumination scheme with an obliquely irradiating through the side of the lens, or use an illumination mode with ring-shaped LEDs surrounding a lens, or use a light guide system to export laser light around a lens in a continuously annular manner for illumination. Shape of a light source appears when a working distance is relatively short, then it is impossible to cover the entire field of view. A light beam is offset from a central uniform area when the working distance is relatively long, then excitation light power density within the field of view is not uniform. Therefore, all the illumination modes in the related art have the problem of limited effective working distance.

SUMMARY

The present disclosure aims at providing a fluorescence imaging probe and a handheld imaging prober, so that an incident light beam is arranged coaxially with an image detector, thereby a working distance of the fluorescence imaging probe can be expanded, and the imaging quality of the fluorescence imaging probe can be improved.

An embodiment of the present disclosure provides a fluorescence imaging probe, including a dichroic filter and an image detector, the dichroic filter is arranged at an included angle of 45° with a direction of a main optical axis of incident excitation light, the incident excitation light is reflected by the dichroic filter to a target detection position, the reflected incident excitation light excites a fluorescent substance at the target detection position to form fluorescence, a main optical axis of the fluorescence is arranged coaxially with the image detector, the fluorescence is incident to the image detector through the dichroic filter, and the image detector converts the received fluorescence into an image signal.

As an optional embodiment, the incident excitation light is emitted by a laser device and transmitted to the dichroic filter through optical fiber, a dodging lens group is further provided at a light emergent side of the optical fiber, the dodging lens group includes a diverging element and a dodging lens that are arranged in sequence, the diverging element is configured to diffuse a divergence angle of the incident excitation light, and the dodging lens is configured to homogenize the diffused incident excitation light.

As an optional embodiment, setting parameters in the dodging lens group satisfy the following relationships:

$$\begin{cases} \tan\theta_1 = \dfrac{u \tan\theta_0}{-v} \\ d = u - \dfrac{\phi}{2\tan\theta_0} \\ D > 2u \tan\theta_0 \end{cases}$$

where u is a distance between a laser light emitting point and the diverging element, v is a distance between the dodging lens and the diverging element, $\theta_0$ is a half divergence angle of the incident excitation light at the light emergent side of the optical fiber, $\theta_1$ is a half divergence angle of the diverging element, $\emptyset$ is a diameter of the optical fiber, D is a clear aperture of the diverging element, and d is a distance between the light emergent side of the optical fiber and the diverging element.

As an optional embodiment, an optical adapter is further provided at the light emergent side of the dichroic filter, and the fluorescence passes through the dichroic filter, and is incident to the image detector after being converged by the optical adapter at the light emergent side of the dichroic filter.

As an optional embodiment, the fluorescence imaging probe further includes a supplementing light source arranged at a light incident side of the optical fiber, the supplementing light source is configured to emit white light, a dichroic element and a long-wave-pass filter element are further provided in sequence at the light emergent side of the optical fiber, a light guide bundle is further provided at a reflection side of the dichroic element, the light guide bundle extends to a direction away from the dichroic element and is wound around a light exit of the fluorescence imaging probe, a light beam emitted from the supplementing light source, after propagating in the optical fiber, is incident to the dichroic element and is reflected into the light guide bundle, so as to form annular illumination at the light exit of the fluorescence imaging probe, and the incident excitation light passes through the dichroic element and the long-wave-pass filter element and then is incident to the dichroic filter.

As an optional embodiment, a first optical filter is provided at the light emergent side of the dichroic filter, and the first optical filter is configured to filter out scattered light in emergent fluorescence.

As an optional embodiment, a first planar reflecting mirror and a second planar reflecting mirror are provided at intervals in sequence at a light reflecting side of the dichroic filter, the first planar reflecting mirror is perpendicular to the dichroic filter, and the second planar reflecting mirror and the first planar reflecting mirror have a preset included angle therebetween, the preset included angle is 15°-35°, the incident excitation light reflected by the dichroic filter is reflected by the first planar reflecting mirror and the second planar reflecting mirror and then is emitted.

As an optional embodiment, a light splitting prism and a second optical filter are further provided at a receiving side of the image detector, and the light splitting prism separates the white light in the fluorescence and filters out the white light through the second optical filter.

As an optional embodiment, the fluorescence imaging probe further includes a first shell, a light incident channel and a light transmission channel perpendicular to each other are formed in the first shell, the dichroic filter is fixedly provided at an intersection of the light incident channel and the light transmission channel, moreover, the dichroic filter has an included angle of 45° with the light transmission channel, and the optical fiber extends into the light incident channel so that the main optical axis of the incident excitation light has an included angle of 45° with the dichroic filter.

As an optional embodiment, optical glass with high transmittance at 400-900 nm are provided respectively at two ends of the light incident channel, especially high transmittance not lower than 99% for 780-790 nm.

As an optional embodiment, the fluorescence imaging probe further includes a second shell provided at an outer periphery of the optical adapter, the optical adapter includes a converging element, and the converging element is fixedly connected to an inner side wall of the second shell.

As an optional embodiment, the first shell and the second shell are detachably connected.

An embodiment of the present disclosure further provides a handheld imaging prober, wherein the handheld imaging prober includes the above fluorescence imaging probe, and an image display member connected to the image detector of the fluorescence imaging probe, and the image display member receives and displays the image signal of the image detector.

The embodiments of the present disclosure include the following beneficial effects.

The fluorescence imaging probe provided in the present disclosure includes the dichroic filter and the image detector, wherein the dichroic filter is arranged at an included angle of 45° with the direction of the main optical axis of the incident excitation light, the incident excitation light is reflected by the dichroic filter to the target detection position, the reflected incident excitation light excites the fluorescent substance at the target detection position to form the fluorescence, the main optical axis of the fluorescence is arranged coaxially with the image detector, the fluorescence is incident to the image detector through the dichroic filter, so that the fluorescence imaging probe has better imaging quality at any working distance, the image detector converts the received fluorescence into the image signal, thereby the working distance of the fluorescence imaging probe can be expanded, and the imaging quality of the fluorescence imaging probe can be improved.

BRIEF DESCRIPTION OF DRAWINGS

In order to more clearly illustrate technical solutions of embodiments of the present disclosure, drawings which need to be used in the embodiments will be introduced briefly below, and it should be understood that the drawings below merely show some embodiments of the present disclosure, therefore, they should not be considered as limitation to the scope, and a person ordinarily skilled in the art still could obtain other relevant drawings according to these drawings, without using any inventive efforts.

Reference signs: 10—fluorescence imaging probe; 11—dichroic filter; 12—image detector; 13—dodging lens group; 131—diverging element; 132—dodging lens; 14—first optical filter; 151—dichroic element; 152—long-wave-pass filter element; 153—light guide bundle; 161—first planar reflecting mirror; 162—second planar reflecting mirror; 163—light splitting prism; 164—second optical filter; 17—first shell; 18—second shell; 19—optical adapter.

DETAILED DESCRIPTION OF EMBODIMENTS

In order to make objectives, technical solutions, and advantages of the embodiments of the present disclosure clearer, the technical solutions in the embodiments of the present disclosure will be described clearly and completely below with reference to the drawings in the embodiments of the present disclosure. Apparently, the embodiments described are some but not all embodiments of the present disclosure. Generally, components in the embodiments of the present disclosure, as described and shown in the drawings herein, may be arranged and designed in various different configurations.

Therefore, the detailed description below of the embodiments of the present disclosure provided in the drawings is not intended to limit the scope of the present disclosure claimed, but merely illustrates chosen embodiments of the present disclosure. All of other embodiments obtained by those ordinarily skilled in the art based on the embodiments of the present disclosure without using any inventive efforts shall fall within the scope of protection of the present disclosure.

It should be noted that similar reference signs and letters represent similar items in the following drawings, therefore, once a certain item is defined in one drawing, it is not needed to be defined or explained in subsequent drawings.

In the description of the present disclosure, it should be noted that orientation or positional relationships indicated by terms such as "center", "vertical", "horizontal", "inner", and "outer" are based on orientation or positional relationships as shown in the drawings, or orientation or positional relationships of a product of the present disclosure when being conventionally placed in use, merely for facilitating describing the present disclosure and simplifying the description, rather than indicating or suggesting that related devices or elements have to be in the specific orientation or configured and operated in a specific orientation, therefore, they should not be construed as limitation to the present disclosure. Besides, terms such as "first", "second", and "third" are merely for distinguishing the description, but should not be construed as indicating or implying importance in the relativity.

Moreover, the terms "horizontal", "vertical" and the like do not mean that the parts are required to be absolutely horizontal or overhanging, but may be slightly inclined. For example, by "horizontal" it merely means that a structure is more horizontal in comparison with "vertical", rather than being completely horizontal, while the structure can be slightly inclined.

In the description of the present disclosure, it should be further noted that, unless otherwise specifically regulated and defined, the terms "set", "install", "link", and "connect" should be understood in a broad sense, for example, a connection may be a fixed connection, a detachable connection, or an integrated connection; it may be a mechanical connection or an electrical connection; it may be direct joining or indirect joining through an intermediary, and it also may be inner communication between two elements. For those ordinarily skilled in the art, the specific meanings of the above-mentioned terms in the present disclosure could be construed in accordance with specific circumstances.

Fluorescence imaging devices for tumor surgeries have become a research hotspot in precision medical care. Relevant fluorescence imaging navigation devices are substantially divided into two categories according to use: imaging navigation system suitable for open surgeries and endoscopic fluorescence imaging system suitable for minimally invasive surgeries.

The present disclosure provides a fluorescence imaging probe 10, as shown in FIG. 1, FIG. 2, FIG. 3, and FIG. 5, including a dichroic filter 11 and an image detector 12, wherein the dichroic filter 11 is arranged at an included angle of 45° with a direction of a main optical axis of incident excitation light, the incident excitation light is reflected by the dichroic filter 11 to a target detection position, the reflected incident excitation light excites a fluorescent substance at the target detection position to form fluorescence, a main optical axis of the fluorescence is arranged coaxially with the image detector 12, the fluorescence is incident to the image detector 12 through the dichroic filter 11, and the image detector 12 converts the received fluorescence into an image signal.

Figure 1:
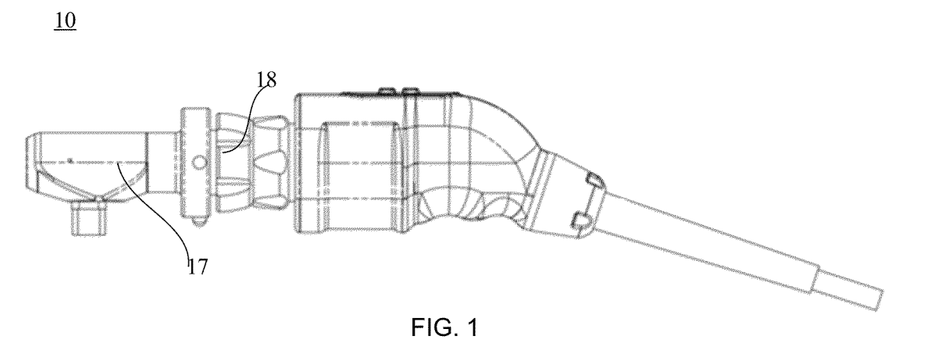
FIG. 1 is a first structural schematic view of a fluorescence imaging probe provided in an embodiment of the present disclosure.
Figure 2:
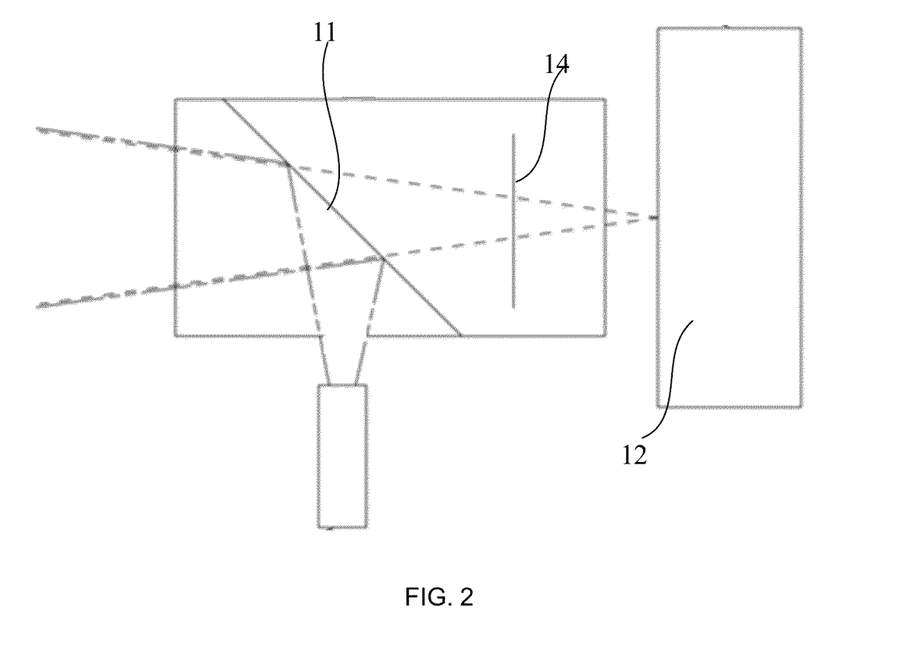
FIG. 2 is an optical path diagram of a fluorescence imaging probe provided in an embodiment of the present disclosure.

A specific optical path of the fluorescence imaging probe 10 is as shown in FIG. 2. The included angle between the main optical axis of the incident excitation light in optical fiber and the dichroic filter 11 is set to be 45°. The dichroic filter 11 has dichroism, and totally reflects light beams with a specific wavelength, and totally transmits light beams with other wavelengths. The dichroic filter 11 in the embodiments of the present disclosure can reflect light with a wavelength of the incident excitation light, and when the incident excitation light excites the fluorescent substance to form the fluorescence, the fluorescence is changed in wavelength, and can be completely transmitted by the dichroic filter 11, and when being incident to the dichroic filter 11, the incident excitation light is reflected and propagates along a straight line to the target detection position, reacts with the fluorescent substance at the target detection position and emits fluorescence. The fluorescence is emitted along an opposite direction of the incident excitation light, and is incident to the image detector 12 through the dichroic filter 11, and the image detector 12 converts the received fluorescence into the image signal to be viewed by an operator.

The main optical axis of the fluorescence is arranged coaxially with the image detector 12, and propagation directions of the fluorescence and the incident excitation light reflected by the dichroic filter 11 are opposite, so that the incident excitation light reflected by the dichroic filter 11 is arranged coaxially with the image detector 12, thus the fluorescence imaging probe 10 has better imaging quality at any working distance.

In the above, a specific structure of the image detector 12 is not limited in the embodiments of the present disclosure, as long as the image detector can convert an optical signal into an image signal. For example, the image detector 12 can be provided as a photosensitive detecting element and an image processing element, wherein the photosensitive detecting element receives the fluorescence and converts the fluorescence into an electrical signal, and the image processing element receives the electrical signal and converts the electrical signal into the image signal. In the above, the photosensitive detecting element may be a CMOS camera or a CCD camera.

Since the photosensitive detecting element needs to receive the fluorescence, the photosensitive detecting element needs to be provided at a predetermined distance from the dichroic filter 11, and in order to make full use of space, the photosensitive detecting element can be provided inside a handle.

For the fluorescence imaging probe 10 provided in the present disclosure, the incident excitation light is reflected by the dichroic filter 11 to the target detection position, the reflected incident excitation light excites the fluorescent substance at the target detection position to form the fluorescence. The main optical axis of the fluorescence is arranged coaxially with the image detector 12, and the fluorescence is incident to the image detector 12 through the dichroic filter 11, so that the fluorescence imaging probe 10 has better imaging quality at any working distance. The image detector 12 converts the received fluorescence into the image signal, thereby the working distance of the fluorescence imaging probe 10 can be expanded, and the imaging quality of the fluorescence imaging probe 10 can be improved.

Figure 3:
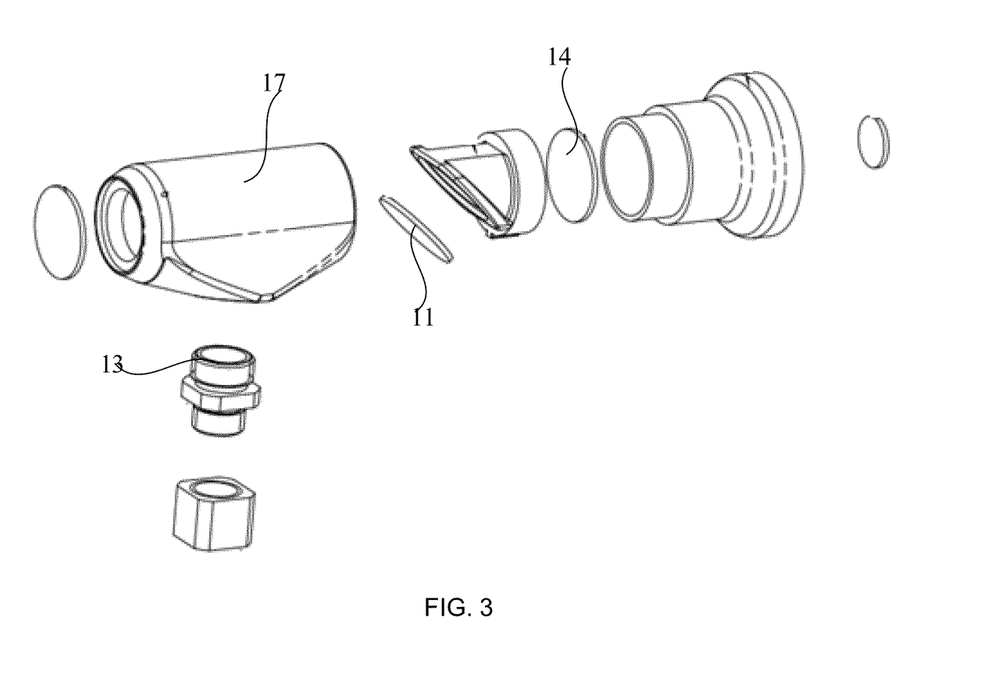
FIG. 3 is an exploded view of a fluorescence imaging probe provided in an embodiment of the present disclosure.

Optionally, as shown in FIG. 3, the incident excitation light is emitted by a laser device and transmitted to the dichroic filter 11 through the optical fiber, and a dodging lens group 13 is further provided at a light emergent side of the optical fiber. The dodging lens group 13 includes a diverging element 131 and a dodging lens 132 that are arranged in sequence, wherein the diverging element 131 is configured to diffuse a divergence angle of the incident excitation light, and the dodging lens 132 is configured to homogenize the diffused incident excitation light.

In the above, the diverging element 131 is configured to diffuse the divergence angle of the incident excitation light, such that the diffused divergence angle is slightly larger than a field angle of the image detector 12, so that the divergence angle of the diffused incident excitation light at the dichroic filter 11 is greater than the field angle of the image detector 12. When the incident excitation light excites to form the fluorescence, the divergence angle of the fluorescence is larger than the field angle of the image detector 12, which enables the fluorescence to be capable of just covering (or be slightly larger than) the field angle of the image detector 12 all the time, regardless of the working distance. Thus, the working distance of the fluorescence imaging probe 10 can be expanded, and the imaging quality of the fluorescence imaging probe 10 can be improved.

Energy in the emitted excitation light after being diffused is not uniform, then in order to make the energy of the incident excitation light uniform, the dodging lens is provided at a light emergent side of the diverging element 131, and the dodging lens 132 is configured to homogenize the diffused incident excitation light, so that the energy in the emitted excitation light after being diffused is uniform.

In the above, a specific structure of the diverging element 131 is not limited in the embodiments of the present disclosure. For example, it may be a convex lens as shown in FIG. 3, or may be a group of lenses cooperating with each other. The dodging lens 132 may be a dodging sheet of a ground glass structure.

Figure 4:
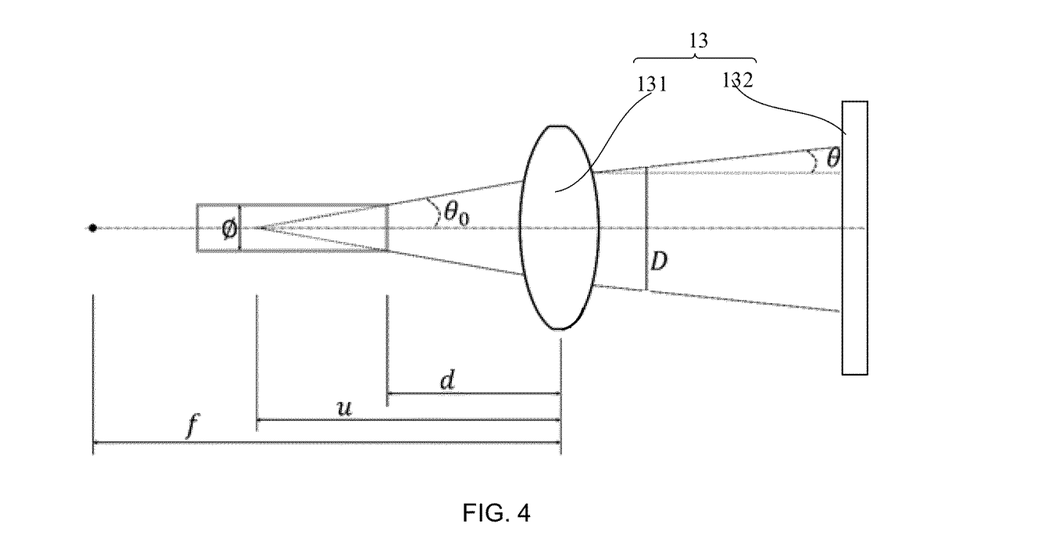
FIG. 4 is a schematic view of a dodging lens group provided in an embodiment of the present disclosure.
Figure 5:
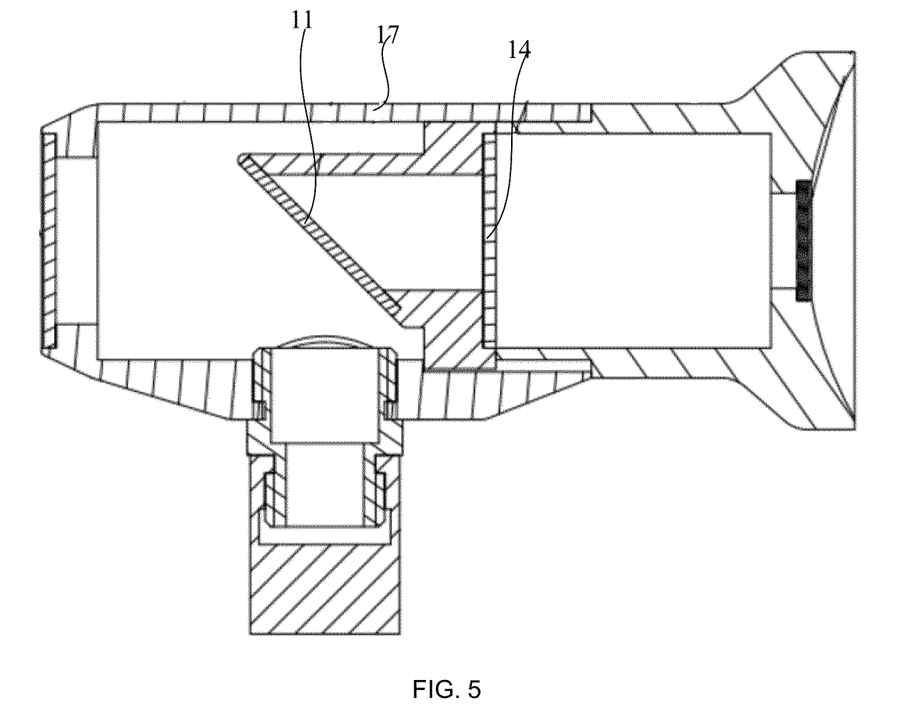
FIG. 5 is a sectional view of a fluorescence imaging probe provided in an embodiment of the present disclosure.

In order to enable the fluorescent to just cover (or be slightly larger than) the field angle of the image detector 12 all the time, as shown in FIG. 4, setting parameters in the dodging lens group 13 satisfy the following relationships:

$$\begin{cases} \tan\theta_1 = \dfrac{u\tan\theta_0}{-v} \\ d = u - \dfrac{\phi}{2\tan\theta_0} \\ D > 2u\tan\theta_0 \end{cases}$$

where u is a distance between a laser light emitting point and the diverging element 131, v is a distance between the dodging lens 132 and the diverging element 131, $\theta_0$ is a half divergence angle of the incident excitation light at the light emergent side of the optical fiber, $\theta_1$ is a half divergence angle of the diverging element 131, Ø is a diameter of the optical fiber, D is a clear aperture of the diverging element 131, and d is a distance between the light emergent side of the optical fiber and the diverging element 131.

Figure 6:
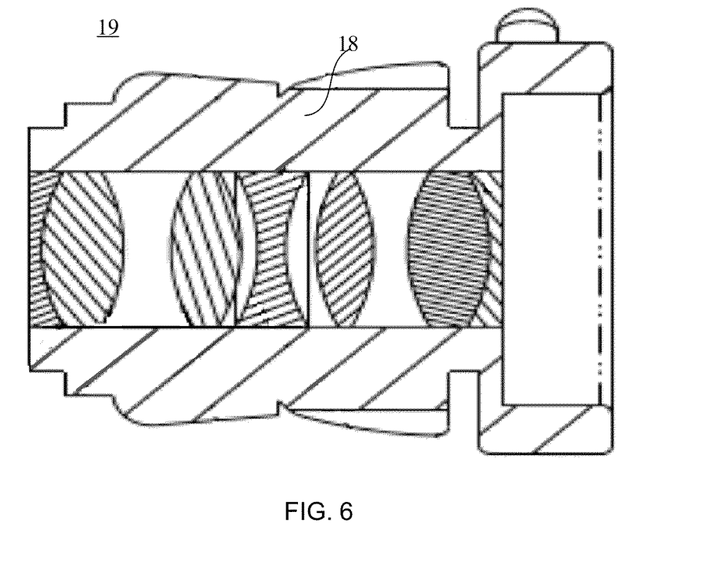
FIG. 6 is a structural schematic view of an optical adapter provided in an embodiment of the present disclosure.

Optionally, as shown in FIG. 6, an optical adapter 19 is further provided at the light emergent side of the dichroic filter 11, and the fluorescence passes through the dichroic filter 11, and is incident to the image detector 12 after being converged by the optical adapter 19 at the light emergent side of the dichroic filter 11.

After the laser light excites the fluorescent substance at the target position to form the fluorescence, the divergence angle of the fluorescence is generally relatively large, and an image formed behind the dichroic filter 11 is also relatively large. In order to be capable of receiving all fluorescence, it is necessary to provide a relatively large photosensitive detecting element, which does not facilitate integration and miniaturization of the fluorescence imaging probe 10. In order to realize reception of all fluorescence with a relatively small photosensitive detecting element, the optical adapter 19 is provided at the light emergent side of the dichroic filter 11 in the embodiments of the present disclosure, then after the optical adapter 19 converges the fluorescence, the divergence angle of the fluorescence is reduced, so that an image formed on the image detector is relatively small, thus the image detector 12 is dimensionally reduced.

In the above, a specific form of the converging element is not limited in the embodiments of the present disclosure, as long as it can play a role of converging the excitation light, and exemplarily, a convex lens may be provided, or as shown in FIG. 6, a group of lenses also may be provided.

Figure 7:
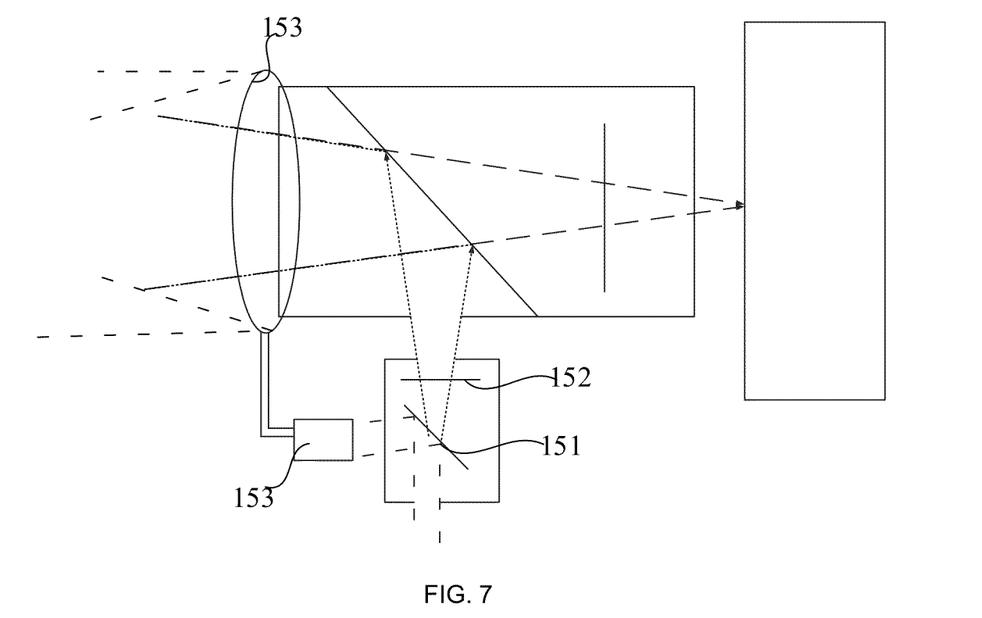
FIG. 7 is a second structural schematic view of a fluorescence imaging probe provided in an embodiment of the present disclosure.

In one implementable mode of the embodiments of the present disclosure, as shown in FIG. 7, the fluorescence imaging probe 10 further includes a supplementing light source arranged at a light incident side of the optical fiber, and the supplementing light source is configured to emit white light. A dichroic element 151 and a long-wave-pass filter element 152 are further provided in sequence at the light emergent side of the optical fiber, a light guide bundle 153 is further provided at a reflection side of the dichroic element 151, and the light guide bundle 153 extends to a direction away from the dichroic element 151 and is wound around a light exit of the fluorescence imaging probe 10. A light beam emitted from the supplementing light source, after propagating in the optical fiber, is incident to the dichroic element 151 and is reflected into the light guide bundle 153, so as to form annular illumination at the light exit of the fluorescence imaging probe 10, and the excitation light passes through the dichroic element 151 and the long-wave-pass filter element 152 and then is incident to the dichroic filter 11.

In general surgeries, a shadowless lamp is usually used for illumination, but in surgeries using the fluorescence imaging, since a process of excitation with laser light to form fluorescence is involved, and the shadowless lamp contains components of fluorescence waveband, interference may be caused to the fluorescence formed. In order to avoid the interference caused by the shadowless lamp to the fluorescence, in the fluorescence imaging surgeries, the shadowless lamp is usually turned off, then there is no illumination light source in surgeries. In the embodiments of the present disclosure, the supplementing light source is provided in the fluorescence imaging probe 10, light emitted from the supplementing light source is white light, and can illuminate the field of view of surgeries.

Specifically, the supplementing light source is provided at the light incident side of the optical fiber, so that the excitation light and the white light share the same optical fiber. The dichroic element 151 and the long-wave-pass filter element 152 are provided in sequence at the light emergent side of the optical fiber. A white light beam emitted from the optical fiber is reflected by the dichroic element 151 and then is incident to the light guide bundle 153, and the light guide bundle 153 extends to a direction away from the dichroic element 151 and is wound around the light exit of the fluorescence imaging probe 10, so as to transmit the white light beam to the light exit of the fluorescence imaging probe 10, and form the annular illumination at the light exit of the fluorescence imaging probe 10.

In addition, since the white light beam emitted from the supplementing light source has a wavelength different from that of the excitation light, the dichroic element 151 can reflect the white light beam and can transmit the excitation light. The excitation light passes through the dichroic element 151 and the long-wave-pass filter element and then is incident to the dichroic filter 11, so that the dichroic element 151 will not affect the transmission of the excitation light, and moreover, the long-wave-pass filter element 152 further can filter out the white light mixed into the excitation light, thereby avoiding the influence of the white light on the conduction of laser light and imaging artifacts.

Optionally, a first optical filter 14 is provided at the light emergent side of the dichroic filter 11, and the first optical filter 14 is configured to filter out scattered light in the emergent fluorescence.

Those skilled in the art would appreciate that when fluorescence passes through the dichroic filter 11 to the image detector 12, Rayleigh scattering sometimes will occur, which results in that the fluorescence cannot accurately feed a situation at the target detection position back. In order to filter out Rayleigh scattering, in the embodiments of the present disclosure, the first optical filter 14 is provided at the light emergent side of the dichroic filter 11. The first optical filter 14 is configured to filter out scattered light in the emergent fluorescence, thereby improving specificity to fluorescence imaging and sensitivity to weak fluorescence.

Figure 8:
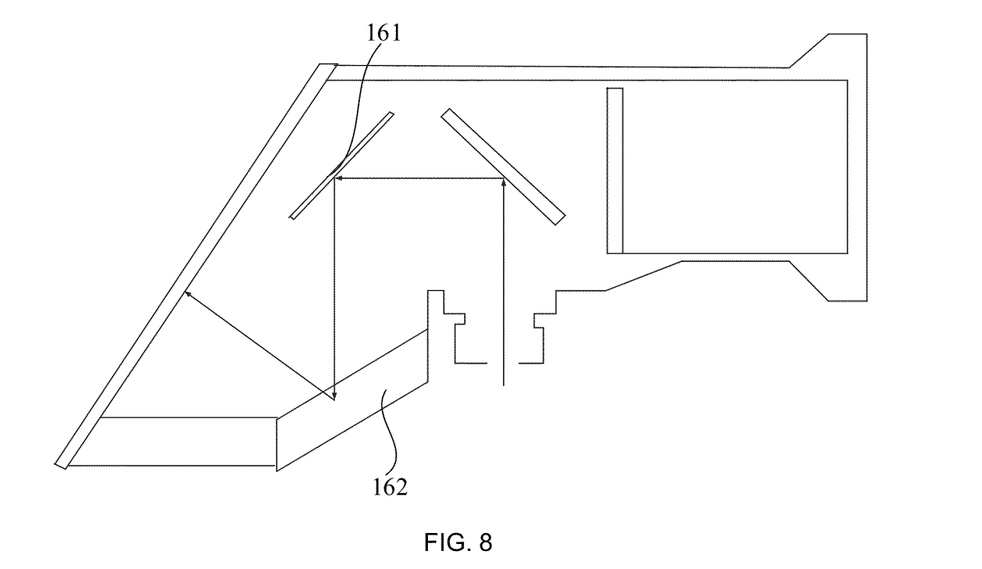
FIG. 8 is a third structural schematic view of a fluorescence imaging probe provided in an embodiment of the present disclosure.

In an implementable mode of the embodiments of the present disclosure, as shown in FIG. 8, a first planar reflecting mirror 161 and a second planar reflecting mirror 162 are provided at intervals in sequence at a light reflecting side of the dichroic filter 11. The first planar reflecting mirror 161 is perpendicular to the dichroic filter 11, and the second planar reflecting mirror 162 and the first planar reflecting mirror 161 have a preset included angle of 15°-35° therebetween. The excitation light reflected by the dichroic filter 11 is reflected by the first planar reflecting mirror 161 and the second planar reflecting mirror 162 and then is emitted.

Because the fluorescence is arranged coaxially with the image detector 12, when the image detector 12 includes the photosensitive detecting element, and the photosensitive detecting element is provided in the handle, the fluorescence is parallel to the handle. On this basis, when a target position in a vertical direction is observed with the fluorescence imaging probe 10, the operator needs to turn over wrist by a relatively large angle, thus the operation difficulty of the operator is increased, and long-time holding will increase the fatigue degree of the operator. In the embodiments of the present disclosure, the first planar reflecting mirror 161 and the second planar reflecting mirror 162 are provided at the light reflecting side of the dichroic filter 11, wherein the first planar reflecting mirror 161 is perpendicular to the dichroic filter 11, and the second planar reflecting mirror 162 and the first planar reflecting mirror 161 have 15°-35° therebetween. The excitation light emitted from the dichroic filter 11 in the horizontal direction, after being reflected by the first planar reflecting mirror 161, is turned by 90° and forms the excitation light in the vertical direction to be incident to the second planar reflecting mirror 162, and the second planar reflecting mirror 162 reflects the excitation light in the vertical direction and then emits the same. As the second planar reflecting mirror 162 and the first planar reflecting mirror 161 have 15°-35° therebetween, the excitation light is emitted obliquely upwards, and with use of two planar reflecting mirrors, the emitted excitation light is coaxial with the field of view and has an included angle of 30°-70° with the horizontal direction, thereby reducing the operation difficulty and the fatigue degree due to long-time holding with hand. Besides, the mirror effect of the image is eliminated after being mirrored twice, and then an image obtained is consistent with a real object in upper, lower, left, and right directions, thus facilitating the observation.

Figure 9:
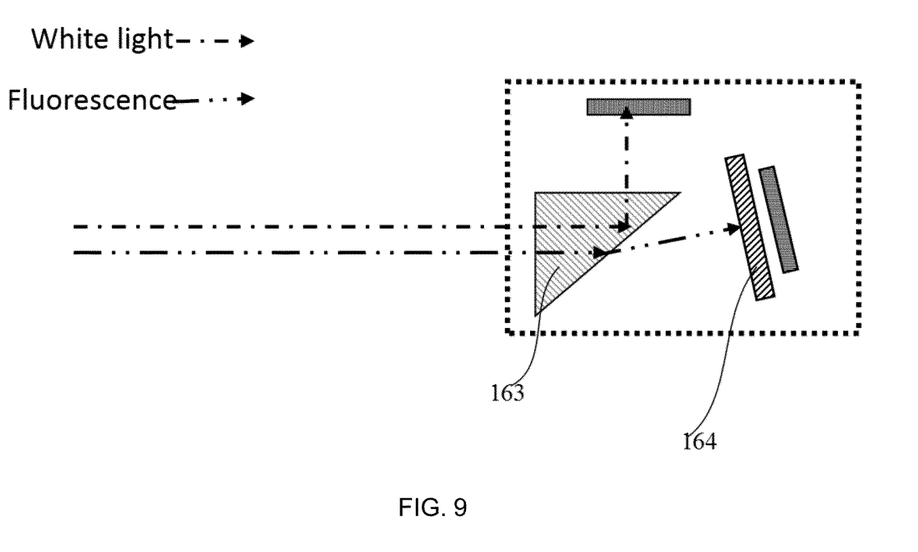
FIG. 9 is a fourth structural schematic view of a fluorescence imaging probe provided in an embodiment of the present disclosure.

Optionally, as shown in FIG. 9, a light splitting prism 163 and a second optical filter 164 are further provided at a receiving side of the image detector 12, and the light splitting prism 163 separates the white light in the fluorescence and filters out the white light through the second optical filter 164.

It can be seen from the foregoing that, in order to provide illumination for surgeries, the supplementing light source is provided. However, in the transmission of the white light, the white light emitted from the supplementing light source is inevitably transmitted to the image detector 12, and received by the image detector 12, thus affecting the accurate transmission of the fluorescence to a target detection object. In order to avoid occurrence of the above situation, in the embodiments of the present disclosure, the light splitting prism 163 and the second optical filter 164 are further provided at the receiving side of the image detector 12, and the light splitting prism 163 separates the white light in the fluorescence and filters out the white light through the second optical filter 164, thereby preventing the white light from being incident to the image detector 12 to affect the accurate transmission of the target detection object by the fluorescence.

In an implementable mode of the embodiments of the present disclosure, the fluorescence imaging probe 10 further includes a first shell 17, in which a light incident channel and a light transmission channel perpendicular to each other are formed. The dichroic filter 11 is fixedly provided at an intersection of the light incident channel and the light transmission channel, and the dichroic filter 11 has an included angle of 45° with the light transmission channel. The optical fiber extends into the light incident channel so that the main optical axis of the incident excitation light has an included angle of 45° with the dichroic filter 11.

In order to fix positions of the dichroic filter 11, the first optical filter 14, and the optical fiber, and improve the stability of the fluorescence imaging probe 10, in an embodiment of the present disclosure, the dichroic filter 11, the first optical filter 14, and the optical fiber are provided in the same shell, so that the fluorescence imaging probe 10 is modularized, thereby facilitating replacement or detachment.

In addition, in order to improve use safety and service lifetime of the fluorescence imaging probe 10, high-transmittance optical glass can be provided respectively at two ends of the light incident channel, so as to prevent external impurities from falling into the light incident channel to damage internal components, thereby functioning to protect the fluorescence imaging probe 10. The high-transmittance optical glass has relatively high transmittance, and will not affect the transmission of laser light, fluorescence, or white light.

Optionally, as shown in FIG. 6, the fluorescence imaging probe 10 further includes a second shell 18 provided at an outer periphery of the optical adapter 19, wherein the optical adapter 19 includes the converging element, and the converging element is fixedly connected to an inner side wall of the second shell 18. For the stability of the optical adapter 19, the second shell 18 is provided, and the converging element is fixedly connected to the inner side wall of the second shell 18.

In an implementable mode of the embodiments of the present disclosure, the first shell 17 is detachably connected to the second shell 18.

In practical applications, in some surgeries, not only open fluorescence imaging device but also endoscopic fluorescence imaging device are required, that is, one device can be easily switched between the open type and the endoscopic type, to meet the requirement of one device with two purposes. In the embodiments of the present disclosure, the first shell 17 is detachably connected to the second shell 18, then when it is required to switch to the endoscopic type, it only needs to detach the first shell 17 from the second shell 18, and connect an endoscope to connection ends of the second shell 18 and the first shell 17, thereby meeting flexible requirements for multiple surgical styles in the same surgery.

In the above, a connection manner of the first shell 17 and the second shell 18 is not limited in the embodiments of the present disclosure, for example, a threaded connection or a snap-fit connection may be used, and connection ends of the endoscope and the first shell 17 should be of the same structure, so that they can be connected to the connection end of the second shell 18 respectively.

An embodiment of the present disclosure further discloses a handheld imaging prober, including the above fluorescence imaging probe 10 and an image display member connected to the image detector 12 of the fluorescence imaging probe 10, wherein the image display member receives and displays the image signal of the image detector 12. The handheld imaging prober has the same structure and beneficial effects as the fluorescence imaging probe 10 in the preceding embodiments. The structure and beneficial effects of the fluorescence imaging probe 10 have been described in detail in the preceding embodiments, and are not described herein again.

The above-mentioned are merely for preferred embodiments of the present disclosure and not used to limit the present disclosure, and for those skilled in the art, various modifications and changes may be made to the present disclosure. Any modifications, equivalent substitutions, improvements and so on, within the spirit and principle of the present disclosure, should be covered within the scope of protection of the present disclosure.

INDUSTRIAL APPLICABILITY

The fluorescence imaging probe provided in the present disclosure includes the dichroic filter and the image detector. The dichroic filter is arranged at an included angle of 45° with the direction of the main optical axis of the incident excitation light. The incident excitation light is reflected by the dichroic filter to the target detection position, and the reflected incident excitation light excites the fluorescent substance at the target detection position to form the fluorescence. The main optical axis of the fluorescence is arranged coaxially with the image detector, and the fluorescence is incident to the image detector through the dichroic filter, so that the fluorescence imaging probe has better imaging quality at any working distance. The image detector converts the received fluorescence into the image signal, thereby the working distance of the fluorescence imaging probe can be expanded, and the imaging quality of the fluorescence imaging probe can be improved.

Besides, it can be understood that the fluorescence imaging probe and the handheld imaging prober of the present disclosure can be reproduced, and can be used in a variety of industrial applications. For example, the fluorescence imaging probe and the handheld imaging prober in the present disclosure can be used in the technical field of medical devices.

What is claimed is:

1. A handheld fluorescence imaging probe, wherein the handheld fluorescence imaging probe comprises a dichroic filter and an image detector,
   wherein the dichroic filter is arranged at an included angle of 45° with a direction of a main optical axis of an incident excitation light;
   the incident excitation light is reflected by the dichroic filter to a target detection position;
   the reflected incident excitation light excites a fluorescent substance at the target detection position to form a fluorescence;
   a main optical axis of the fluorescence is arranged coaxially with the image detector;
   the fluorescence is incident to the image detector through the dichroic filter, and the image detector converts the received fluorescence into an image signal;
   wherein the incident excitation light is emitted by a laser device and transmitted to the dichroic filter through an optical fiber, a dodging lens group is further provided at a light emergent side of the optical fiber, the dodging lens group comprises a diverging element and a dodging lens that are arranged in sequence;
   wherein the dodging lens is configured to homogenize the diffused incident excitation light, and the diverging element is configured to diffuse a divergence angle of the incident excitation light, such that the diffused divergence angle is slightly larger than a field angle of the image detector;
   wherein setting parameters in the dodging lens group satisfy following relationships:

$$\begin{cases} \tan\theta_1 = \dfrac{u\tan\theta_0}{-v} \\ d = u - \dfrac{\phi}{2\tan\theta_0} \\ D > 2u\tan\theta_0 \end{cases}$$

where u is a distance between a laser light emitting point and the diverging element, v is an image distance of the diverging element, $\theta_0$ is a half divergence angle of the incident excitation light at the light emergent side of the optical fiber, $\theta_1$ is a half divergence angle of the diverging element, Ø is a diameter of the optical fiber, D is a clear aperture of the diverging element, and d is a distance between the light emergent side of the optical fiber and the diverging element,
   wherein a first planar reflecting mirror and a second planar reflecting mirror are provided at intervals in sequence at a light reflecting side of the dichroic filter, wherein the first planar reflecting mirror is perpendicular to the dichroic filter, and the second planar reflecting mirror and the first planar reflecting mirror have a preset included angle therebetween, wherein the preset included angle is 15°-35°, and the incident excitation light reflected by the dichroic filter is reflected sequentially by the first planar reflecting mirror and the second planar reflecting mirror and then is emitted, such that the excitation light is coaxial with a field of view and is emitted obliquely upwards at an included angle of 30°-70° with a horizontal direction.

2. The handheld fluorescence imaging probe according to claim 1, wherein an optical adapter is further provided at a light emergent side of the dichroic filter, and the fluorescence passes through the dichroic filter, and is incident to the image detector after being converged by the optical adapter at the light emergent side of the dichroic filter.

3. The handheld fluorescence imaging probe according to claim 1, wherein the handheld fluorescence imaging probe further comprises a supplementing light source arranged at a light incident side of the optical fiber, and the supplementing light source is configured to emit a white light; a dichroic element and a long-wave-pass filter element are further provided in sequence at the light emergent side of the optical fiber; a light guide bundle is further provided at a reflection side of the dichroic element, wherein the light guide bundle extends to a direction away from the dichroic element and is wound around a light exit of the handheld fluorescence imaging probe; a light beam emitted from the supplementing light source, after propagating in the optical fiber, is incident to the dichroic element and is reflected into the light guide bundle, so as to form an annular illumination at the light exit of the handheld fluorescence imaging probe; and the incident excitation light passes through the dichroic element and the long-wave-pass filter element and then is incident to the dichroic filter.

4. The handheld fluorescence imaging probe according to claim 1, wherein a first optical filter is provided at a light emergent side of the dichroic filter, and the first optical filter is configured to filter out a scattered light in an emergent fluorescence.

5. The handheld fluorescence imaging probe according to claim 1, wherein a light splitting prism and a second optical filter are further provided at a receiving side of the image detector, and the light splitting prism separates a white light in the fluorescence and filters out the white light through the second optical filter.

6. The handheld fluorescence imaging probe according to claim 2, wherein the handheld fluorescence imaging probe further comprises a first shell, a light incident channel and a light transmission channel perpendicular to each other are formed in the first shell, wherein the dichroic filter is fixedly provided at an intersection of the light incident channel and the light transmission channel, and the dichroic filter has an included angle of 45° with the light transmission channel; and the optical fiber extends into the light incident channel so that the main optical axis of the incident excitation light has an included angle of 45° with the dichroic filter.

7. The handheld fluorescence imaging probe according to claim 6, wherein the handheld fluorescence imaging probe further comprises a second shell provided at an outer periphery of the optical adapter, the optical adapter comprises a converging element, and the converging element is fixedly connected to an inner side wall of the second shell.

8. The handheld fluorescence imaging probe according to claim 7, wherein the first shell and the second shell are detachably connected.

9. A handheld imaging prober, wherein the handheld imaging prober comprises the handheld fluorescence imaging probe according to claim 1, and an image display member connected to the image detector of the handheld fluorescence imaging probe, and the image display member receives and displays the image signal of the image detector.

* * * * *